US012551696B2

(12) United States Patent
Chandrashekharan et al.

(10) Patent No.: US 12,551,696 B2
(45) Date of Patent: Feb. 17, 2026

(54) ELECTRODES WITH USABILITY INDICATOR

(71) Applicant: Stryker Corporation, Kalamazoo, MI (US)

(72) Inventors: Adithya Chandrashekharan, Portage, MI (US); Aaron Furman, Kalamazoo, MI (US); Scott Batzer, Plainwell, MI (US); Michael Baran, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 371 days.

(21) Appl. No.: 18/184,942

(22) Filed: Mar. 16, 2023

(65) Prior Publication Data

US 2023/0293885 A1 Sep. 21, 2023

Related U.S. Application Data

(60) Provisional application No. 63/320,298, filed on Mar. 16, 2022.

(51) Int. Cl.

| | |
|---|---|
| ***A61N 1/00*** | (2006.01) |
| ***A61N 1/06*** | (2006.01) |
| ***A61N 1/39*** | (2006.01) |

(52) U.S. Cl.
CPC ............. *A61N 1/06* (2013.01); *A61N 1/3925* (2013.01)

(58) Field of Classification Search
CPC ...... A61N 1/06; A61N 1/3925; A61N 1/0472; A61N 1/3904; A61N 1/3993; A61N 1/046
See application file for complete search history.

(56) References Cited

U.S. PATENT DOCUMENTS

| | | | | |
|---|---|---|---|---|
| 5,593,426 A * | 1/1997 | Morgan | A61N 1/3904 128/903 |
| 5,645,571 A * | 7/1997 | Olson | A61N 1/3931 607/142 |
| 5,879,374 A * | 3/1999 | Powers | A61N 1/3931 607/5 |
| 8,532,768 B2 | 9/2013 | Doerr | |
| 11,065,466 B2 | 7/2021 | Quan et al. | |

OTHER PUBLICATIONS

Zoll Medical Corporation, “Fully Automatic AED Plus Administrator’s Guide,” Ref 9650-0311-05 Rev. B, Nov. 1, 2013; 52 pages.

* cited by examiner

*Primary Examiner* — Scott M. Getzow
(74) *Attorney, Agent, or Firm* — Lee & Hayes, P.C.

(57) ABSTRACT

Electrodes having a usability indicator to indicate a usability of the electrodes are described. The electrodes include a first electrode and a second electrode, as well as an output device(s) that are configured to output a usability indication indicative of a usability of the set of electrodes. If the usability indication indicates that the electrodes should be replaced, the user can discard the set of electrodes and replace them with a new set of electrodes, thereby mitigating the risk of compromising patient care for a patient.

20 Claims, 8 Drawing Sheets

ELECTRODES WITH USABILITY INDICATOR

CROSS-REFERENCE TO RELATED APPLICATION

This application claims the benefit of U.S. Provisional Application No. 63/320,298, titled "ELECTRODES WITH USABILITY INDICATOR" and filed on Mar. 16, 2022, and which is incorporated by reference herein in its entirety.

BACKGROUND

Electrodes are usable with a defibrillator to administer defibrillation therapy to a patient. For example, a user can attach electrodes to an external surface of a patient, and the defibrillator delivers electrical shocks to the patient via the attached electrodes. Such electrodes may travel with the patient, such as when the patient is being transported to a hospital. In these circumstances, the electrodes may be transferred from one defibrillator to another defibrillator while remaining attached to the patient, and this may occur a number of times during the care of the patient.

Electrodes are typically replaced more often than the defibrillator itself. For example, single-use, disposable electrodes are intended to be used to administer defibrillation therapy to a single patient and replaced with a new set of electrodes after a single use. Electrodes can also be discarded due to wear, degradation, expiration, or malfunction. For example, electrodes may be rated to deliver a limited number of shocks and should be replaced once the electrodes have reached this shock limit. As another example, electrodes may have an expiration date and should be replaced upon reaching the expiration date. However, it can be difficult for a user to ascertain whether a given set of electrodes should be discarded, which, in turn, may compromise patient care because such electrodes, if used to administer defibrillation therapy to a patient, may not function properly.

DETAILED DESCRIPTION

Figure 1:
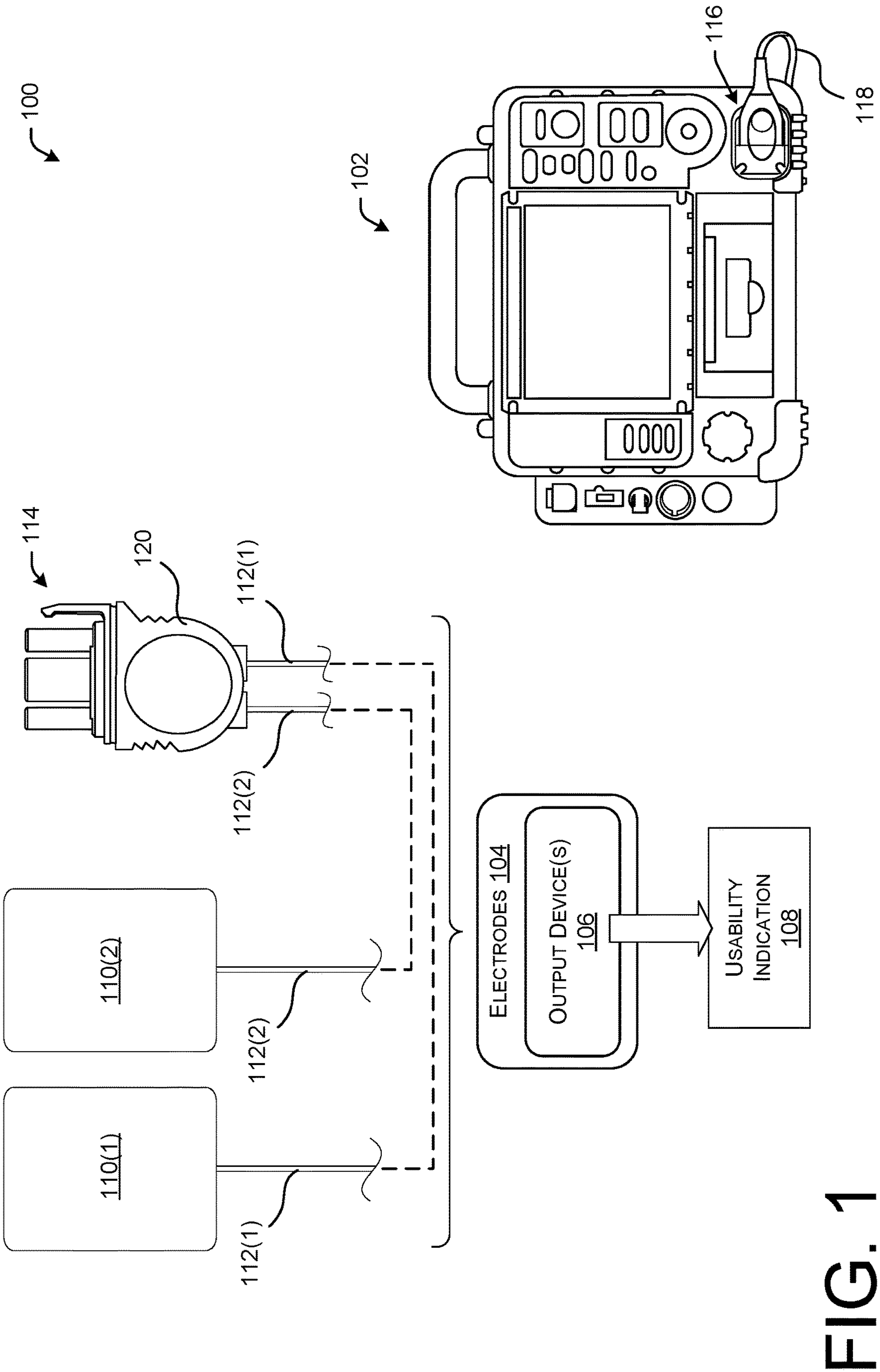
FIG. 1 illustrates an example system including a medical device and a set of electrodes, the set of electrodes including an output device(s) configured to output a usability indication indicative of a usability of the set of electrodes, according to the techniques described herein.

This disclosure provides electrodes having a usability indicator to indicate a usability of the electrodes. In an example, a set of electrodes includes a first electrode and a second electrode, each configured to attach to an external surface of a patient. The set of electrodes is configured to be used with a medical device, such as an external defibrillator. In an example, a user couples the set of electrodes to a medical device (e.g., via an electrode connector of the set of electrodes), attaches the first and second electrodes to an external surface of a patient, and uses the electrodes in conjunction with the medical device. In an example where the medical device is an external defibrillator, the electrodes can be used to administer defibrillation therapy, such as by causing the defibrillator to deliver an electrical shock(s) to the patient via the electrodes.

The set of electrodes further includes an output device(s) configured to output a usability indication indicative of a usability of the set of electrodes. In some examples, one of two usability indications can be output: (i) a usability indication that the electrodes are usable, or (ii) a usability indication that the electrodes should be replaced. In some examples, a single usability indication is output, as appropriate, such as a usability indication that the electrodes should be replaced. In other examples, one of more than two usability indications can be output. This disclosure describes various types of output devices and various types of usability indications that can be output by the output device(s). In an illustrative example, the set of electrodes includes an output device in the form of a display that provides the usability indication as a visual indication on the display. It is to be appreciated that another type(s) of output device(s) can be implemented to output another type(s) of usability indication(s).

In some examples, the usability indication that is output by the output device(s) of the set of electrodes is based on a condition(s) of the electrode(s). In this sense, the set of electrodes may include a component(s) configured to "self-assess" the condition(s) of the set of electrodes to determine the usability indication that is to be output to a user. In an example, the set of electrodes may include a processor(s) that is configured to execute instructions (e.g., a shock counter) to count a number of electrical shocks delivered via the set of electrodes, and a usability indication based on the number of the electrical shocks delivered is output by the output device(s) of the set of electrodes. In this example, the condition of the electrode(s) is the number of shocks delivered via the set of electrodes, and the usability indication can be output as the number of shocks delivered. In some examples, the condition of the electrode(s) may be determined by comparing the number of shocks delivered to a threshold. For example, if the number of shocks delivered is less than a threshold number of shocks (e.g., a maximum number of shocks for which the electrodes are rated), the usability indication based on this condition may indicate that the electrodes are usable. On the other hand, if the number of shocks delivered is equal to or greater than the threshold number of shocks, the usability indication based on this condition may indicate that the electrodes should be replaced (or discarded). It is to be appreciated that such electrodes (e.g., electrodes that have reached their shock limit) may still be "usable," even though a manufacturer of the electrodes recommends that they be replaced. That is, a user may still choose to use the electrodes even if the usability indication indicates that the electrodes should be replaced, although it may not be advisable to do so because patient care may be compromised by using such electrodes with the patient, as described herein. It is also to be appreciated that the usability indication can be based on another condition(s) of the electrodes besides, or in addition to, the number of shocks delivered, such as whether the expiration date of the electrodes has been reached, among other example conditions that may factor into the usability indication output by the output device(s) of the electrodes. Furthermore, the output device(s) of the set of electrodes, in some examples, is/are configured to output additional information about the electrodes to assist a user with assessing a condition of the electrodes and/or providing the user with more information about the electrodes and/or the patient.

A user of the set of electrodes can readily determine the usability of the set of electrodes based on the usability indication output by the output device(s) of the set of electrodes. If the usability indication indicates that the set of electrodes should be replaced (or discarded), the user can discard the set of electrodes and replace them with a new set of electrodes, thereby mitigating the risk of compromising patient care for a patient, who may be in need of therapy, such as defibrillation therapy.

The usability indication travels with the electrodes, as opposed to traveling with an external device or system, such as an external defibrillator. In this manner, the usability indication can be output via the output device(s) of the set of electrodes even after a user detaches the electrodes from an associated medical device (e.g., a defibrillator), and while the electrodes are disconnected from the medical device. In other words, the set of electrodes can self-assess its own usability without relying on another device, such as an associated medical device (e.g., a defibrillator), to assess the condition(s) of the set of electrodes. Accordingly, the usability of the set of electrodes can be assessed and output via the output device(s) of the set of electrodes autonomously and independently of an external device or system, such as an external defibrillator. Furthermore, with the disclosed electrodes, a user does not have to manually track, or otherwise determine, information about the set of electrodes that is used to assess the usability of the electrodes. This is because a component(s) of the set of electrodes is/are configured to determine and/or track information used to self-assess a condition(s) of the electrodes, and the output device(s) of the set of electrodes is/are configured to output a usability indication based on the condition(s) of the electrodes, all without user intervention, which mitigates instances of user error.

In an example scenario, a bystander may use a publicly-accessible automated external defibrillator (AED) with the disclosed set of electrodes to deliver a number of electrical shocks to a patient who is experiencing sudden cardiac arrest. Subsequently, or while the electrical shocks are being delivered to the patient via the disclosed electrodes, a crew of emergency medical technicians (EMTs) may arrive on the scene to take over patient care. In this scenario, the disclosed electrodes can be detached from the AED while remaining attached to the external surface of the patient, and the electrodes can be subsequently attached to an external defibrillator that is located in an ambulance, for example. Even after the disclosed electrodes are detached from the publicly-accessible AED, the output device(s) of the disclosed electrodes can output a usability indication so that the crew of EMTs (or anyone else for that matter), at any time during the care of the patient, can readily determine the usability of the set of electrodes. In this example scenario, the crew of EMTs can trust the usability indication, seeing as how it is more reliable than existing methods of determining how many shocks were delivered via the electrodes, such as the bystander who initially helped rescue the patient verbally relaying, to the crew of EMTs, that a certain number of shocks were delivered via the electrodes using the publicly-accessible AED. It can be readily appreciated that such verbally relayed information may be inaccurate, and that the disclosed electrodes provide a more reliable, trustworthy source of ground truth as to the condition(s) of the electrodes. Furthermore, the usability information continues to travel with the electrodes along the chain of custody of the patient, such as when the ambulance arrives at the hospital and the electrodes are transferred to an in-hospital medical device, such as a monitor/defibrillator in an emergency room of the hospital. These and other technical benefits are readily appreciated in light of this disclosure, with detailed reference to the figures provided below.

FIG. 1 illustrates an example system 100 including a medical device 102 and a set of electrodes 104, the set of electrodes 104 including an output device(s) 106 configured to output a usability indication 108 indicative of a usability of the set of electrodes 104, according to the techniques described herein. In some examples, the medical device 102 represents an external defibrillator configured to administer defibrillation therapy to a patient. In some examples, the medical device 102 is a monitor-defibrillator, an automated external defibrillator (AED), or any other type of external device configured to be used in conjunction with the set of electrodes 104 and/or configured to use the set of electrodes 104 as an accessory.

In some examples, the set of electrodes 104 is configured to be used to assist with monitoring a patient, treating a patient, or both monitoring and treating a patient using the medical device 102. In an example, the set of electrodes 104 represents defibrillation electrodes that are configured to deliver an electrical shock (or a defibrillation shock) to a patient. Additionally, or alternatively, the set of electrodes 104 may represent electrocardiogram (ECG) electrodes, or any other suitable type of electrodes. The set of electrodes 104 includes an electrode pad(s) 110 (often shortened herein to "electrode(s) 110"), an electrode lead(s) 112, and an electrode connector 114. Accordingly, any reference herein to "electrodes 104" means an assembly that includes an electrode pad(s) 110, an electrode lead(s) 112, and an electrode connector 114. Any reference herein to "electrodes 110" means the electrode pads 110 disposed at the respective ends of the electrode leads 112. The example of FIG. 1 depicts a pair of electrode pads 110 including a first electrode 110(1) and a second electrode 110(2). It is to be appreciated that the set of electrodes 104 may include fewer electrode pads 110 or a greater number of electrode pads 110 than the pair of electrode pads 110 depicted in FIG. 1.

The first electrode 110(1) is coupled to the electrode connector 114 via the first electrode lead 112(1), and the second electrode 110(2) is coupled to the electrode connector 114 via the second electrode lead 112(2). Said another way, the first electrode lead 112(1) has a first end coupled to the first electrode 110(1), the second electrode lead 112(2) has a first end coupled to the second electrode 110(2), and the electrode connector 114 is coupled to a second end of the first electrode lead 112(1) and to a second end of the second electrode lead 112(2). The electrode leads 112 are sometimes referred to herein as "lead wires 112," "cables 112," "electrode lead wires 112," or "electrode cables 112." The electrode leads 112 are depicted in FIG. 1 with dashed lines in the middle of the leads 112, which indicates that the electrode leads 112 can have a length that is longer than what is depicted in FIG. 1.

The electrode connector 114 is configured to couple to a port 116 of the medical device 102 (e.g., an external defibrillator). In one example, the electrode connector 114 is configured to indirectly couple to the port 116 of the medical device 102 by coupling the electrode connector 114 to a first end of a cable 118, and by coupling a second end of the cable 118 to the port 116 of the medical device 102. It is to be appreciated that the electrode connector 114 may be configured to directly couple to the port 116 of the medical device 102 instead of indirectly coupling to the port 116 via the cable 118. In some examples, the electrode connector 114 includes a housing 120, and a portion of the housing 120 includes a male or female connection element(s) configured to couple to the cable 118 or to the port 116 of the medical device 102. In an example, the electrode connector 114 is configured to be removably coupled to the port 116 of the medical device 102, such as by a user detaching the electrode connector 114 from an end of the cable 118. Elements are permanently coupled if a user or another entity is unable to decouple the elements without destroying or significantly damaging the elements, or without undue effort to disassemble the elements using tools or machinery. In an example, the electrode leads 112 may be permanently coupled to the electrodes 110 and also to the electrode connector 114. As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

Accordingly, the electrode connector 114 allows the first electrode 110(1) to be coupled to the medical device 102 via the first electrode lead 112(1), and the electrode connector 114 also allows the second electrode 110(2) to be coupled to the medical device 102 via the second electrode lead 112(2). The electrodes 110 are also configured to attach to an external surface of a patient. For example, a user may attach an individual electrode 110 to a patient by peeling away a backing or a liner (not shown in FIG. 1) from the electrode 110 to expose an adhesive side of the electrode 110 with gel disposed thereon, and by pressing the adhesive side with the gel against the skin of the patient. In some examples, the electrodes 110 may be stored in a sealed pouch prior to their use, and the user may first open the pouch to remove the electrodes 110 therefrom, and then the user may remove the backings or liners before attaching the electrodes 110 to the external surface of the patient.

As mentioned, the set of electrodes 104 may represent defibrillation electrodes that are configured to deliver an electrical shock (or a defibrillation shock) to a patient. In this example, the medical device 102, such as an external defibrillator, is configured charge a capacitor of the medical device 102 using a power source of the medical device 102, and then discharge energy that is stored in the charged capacitor across the pair of electrodes 110(1) and 110(2) while the electrodes 110 are in contact with the patient's skin. This energy is discharged from the electrodes 110 in the form of an electrical (or defibrillation) shock. For example, the electrodes 110 may be attached to the skin of a patient and located at positions on different sides of the heart of the patient, such that the defibrillation shock is applied across the heart of the patient. The defibrillation shock, in various examples, depolarizes a significant number of heart cells in a short amount of time. The defibrillation shock, for example, interrupts the propagation of the shockable rhythm through the heart. In some examples, the defibrillation shock is 200 Joules (J) or greater with a duration of about 0.015 seconds.

As mentioned, the set of electrodes 104 may, additionally or alternatively, represent other types of electrodes, such as ECG electrodes. In this example, the electrodes 110 are attachable to an external surface of a patient at different locations on the patient, and the medical device 102 is configured to detect relative voltages between the electrodes 110, which are indicative of the electrical activity of the heart of the patient, which may be used to detect arrhythmias or other heart-related conditions. In some examples, the electrodes 110 may be used to determine whether a patient is experiencing a shockable rhythm that is treatable by defibrillation. Examples of shockable rhythms include ventricular fibrillation (VF) and ventricular tachycardia (V-Tach).

As mentioned, the set of electrodes 104 includes an output device(s) 106 configured to output a usability indication 108 indicative of a usability of the set of electrodes 104. This disclosure describes various types of output devices 106 and various types of usability indications 108 that can be output by the output device(s) 106. In some examples, the usability indication 108 is based on a condition(s) of the electrode(s) 104, and a component(s) of the set of electrodes 104 may be configured to assess the condition(s) to determine whether to output the usability indication 108 and/or what type of usability indication 108 to output. In an example, and as described in more detail below, the set of electrodes 104 includes a processor(s) that is configured to execute instructions (e.g., a shock counter) to count a number of electrical shocks delivered via the set of electrodes 104, and the usability indication 108 that is output by the output device(s) 106 of the set of electrodes 104 is based on the number of the electrical shocks delivered via the set of electrodes 104.

In some examples, if the number of shocks delivered is less than a threshold number of shocks (e.g., a maximum number of shocks for which the electrodes 104 are rated), the usability indication 108 may indicate that the electrodes 104 are usable. On the other hand, if the number of shocks delivered is equal to or greater than the threshold number of shocks, the usability indication 108 may indicate that the electrodes should be replaced (or discarded). In other words, if the electrodes 104 have reached their shock limit, a manufacturer of the electrodes 104 may recommend against using the electrodes 104, and the usability indication 108 may serve the purpose of indicating this manufacturer's recommendation to a user. For example, electrodes 104 that have reached their shock limit (e.g., by having delivered a number of shocks equal to or greater than the maximum number of shocks for which the electrodes 104 are rated) may compromise the care of a patient, and, therefore, the usability indication 108 may be interpreted by a user of the electrodes 104 as an indication that the electrodes 104 should be replaced in order to mitigate the risk of compromising patient care. Besides, or in addition to, the number of shocks delivered, the usability indication 108 can be based on another condition(s) of the electrodes 104, such as a cumulative amount of energy delivered via the electrical shocks, an expired or unexpired condition of the electrodes 104 (e.g., whether a current date coincides with, or is past, an expiration date of the electrodes 104), a condition of the gel disposed on the electrodes 110, a condition of an electronic component(s) of the set of electrodes 104, or any other condition(s) of the electrodes 104 that may factor into the usability of the electrodes 104.

Figure 2:
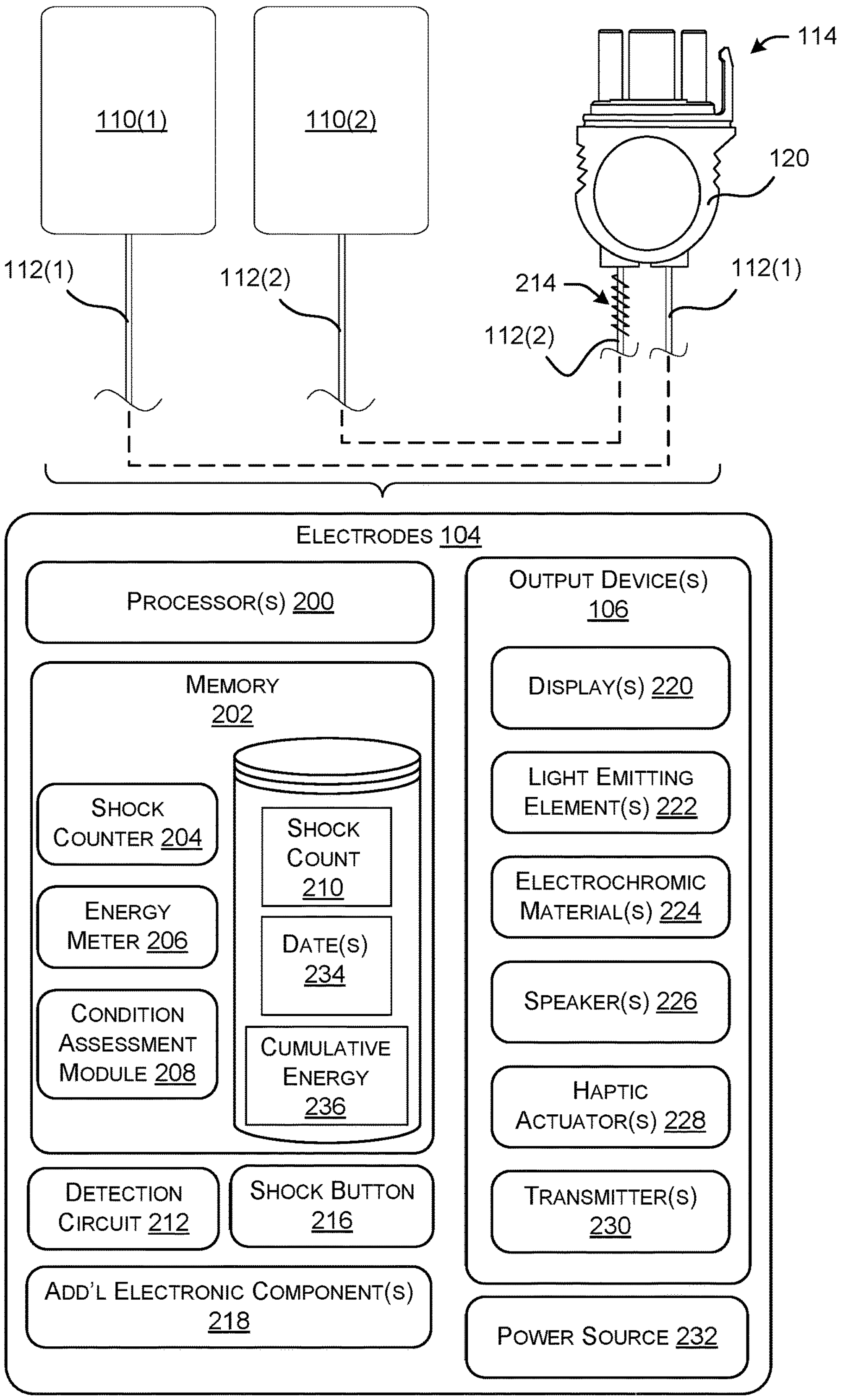
FIG. 2 illustrates example components of a set of electrodes, the components including an output device(s) configured to output a usability indication indicative of a usability of the set of electrodes, according to the techniques described herein.

FIG. 2 illustrates example components of a set of electrodes 104. Among other components, the components include an output device(s) 106 configured to output a usability indication 108 indicative of a usability of the set of electrodes 104, according to the techniques described herein. Individual ones of the components depicted in FIG. 2 may be disposed at (e.g., on or in) the electrode connector 114, at (e.g., on or in) the electrode pads 110, or at (e.g., on or in) the electrode leads 112. Components of the electrodes 104 that are disposed at the electrode connector 114 may be disposed on or in the housing 120 of the electrode connector 114. Furthermore, individual components depicted in FIG. 2 may be hardware components, firmware components, and/or software components.

In some examples, the set of electrodes 104 includes a processor(s) 200, which may be disposed within the housing 120 of the electrode connector 114. In some examples, the processor(s) 200 includes a central processing unit (CPU), a graphics processing unit (GPU), both CPU and GPU, or another processing unit or component known in the art. The processor(s) 200 is operably connected to memory 202, which may be disposed within the housing 120 of the electrode connector 114. In various implementations, the memory 202 is volatile (such as random access memory (RAM)), non-volatile (such as read only memory (ROM), flash memory, etc.) or some combination of the two. The memory 202 stores instructions that, when executed by the processor(s) 200, cause the processor(s) 200 to perform various operations described herein. In various examples, the memory 202 stores methods, threads, processes, applications, objects, modules, any other sort of executable instruction, or a combination thereof. Examples depicted in FIG. 2 include a shock counter 204, an energy meter 206, and a condition assessment module 208. In some cases, the memory 202 stores files, databases, or a combination thereof. In some examples, the memory 202 includes RAM, ROM, electrically erasable programmable read-only memory (EEPROM), flash memory, or any other memory technology. In some examples, the memory 202 includes CD-ROMs, digital versatile discs (DVDs), content-addressable memory (CAM), and/or other optical storage, magnetic cassettes, magnetic tape, magnetic disk storage and/or other magnetic storage devices, and/or any other medium (e.g., non-transitory computer-readable medium) which can be used to store the desired information and which can be accessed by the processor(s) 200 and/or the set of electrodes 104.

As described above, the electrodes 104 may represent defibrillation electrodes configured to deliver defibrillation therapy to a patient in the form of electrical shocks (or defibrillation shocks). In some examples, the processor(s) 200 is configured to determine, using a detection circuit 212, that an electrical shock has been delivered via the set of electrodes 104. Furthermore, the processor(s) 200 is configured to execute the shock counter 204 (e.g., computer-executable instructions) to count a number of the electrical shocks delivered via the set of electrodes 104. For example, the processor(s) 200 may execute the shock counter 204 to keep track of a running count of electrical shocks delivered, and, for each additional shock delivered, the processor(s) 200 may execute the shock counter 204 to increment the shock count 210. FIG. 2 shows that the memory 202 may store the shock count 210 (e.g., the number of shocks delivered via the set of electrodes 104), as determined by the processor(s) 200 executing the shock counter 204.

The shock count 210 may represent, or include, an overall, or total, number of shocks delivered via the set of electrodes 104. In some examples, the shock count 210 is broken down into categories, such as a number of shocks delivered via the set of electrodes 104 at a particular energy level. For example, the medical device 102, such as an external defibrillator, may be configured to deliver shocks at different energy levels, such as a first energy level for adult patients, and at a second energy level for pediatric patients, wherein the second energy level is less than the first energy level. Accordingly, the shock count 210 may include a first number of shocks delivered by the electrodes 104 at the first energy level, a second number of shocks delivered by the electrodes 104 at a second energy level, and so on, for any number of different energy levels at which shocks can be delivered. Other categorizations, or sub-counts, are possible besides, or in addition to, energy level, such as categorizing the number of shocks delivered per defibrillator in a scenario where the set of electrodes 104 are transferred from one defibrillator to another defibrillator(s). That is, the shock count 210 may include a first number of shocks delivered via the electrodes 104 by a first defibrillator, a second number of shocks delivered via the electrodes 104 by a second defibrillator, and so on, for any number of different defibrillators that delivered shocks via the electrodes 104.

In some examples, the set of electrodes 104 includes a detection circuit 212, which may be disposed within the housing 120 of the electrode connector 114. In some examples, the detection circuit 212 is configured to detect a change in an electrical parameter(s) associated with a coil 214 that is disposed around one of the electrode leads 112. FIG. 2 depicts a coil 214 that is wrapped (or wound) around the second electrode lead 112(2), but it is to be appreciated that the coil 214, or an additional coil, may be wrapped (or wound) around the first electrode lead 112(1). In an example, the detection circuit 212 is configured to detect a change in electrical current associated with the coil 214 as a proxy for detecting that a shock has been delivered via the electrodes 104. Additionally, or alternatively, the detection circuit 212 may be configured to detect a change in voltage (a voltage change) associated with the coil 214 as a proxy for detecting that a shock has been delivered via the electrodes 104.

In this manner, the processor(s) 200 may passively detect when an electrical shock is delivered via the electrodes 104 based on an induced electrical current in the coil 214, as detected by the detection circuit 212. For example, when an electrical shock originating from the medical device 102 is delivered via the set of electrodes 104, electrical current flows through the electrode leads 112, which generates a magnetic field around the coil 214, and the magnetic field induces an electrical current in the coil 214. This induced electrical current (and/or a corresponding voltage change) is detectable by the detection circuit 212, which may be coupled to the coil 214. This change in the electrical parameter(s) (e.g., electrical current, voltage, etc.) associated with the coil 214 can be used as a proxy to determine that an electrical shock has been delivered via the electrodes 104. This approach to detecting delivery of an electrical shock is sometimes referred to herein as an electromagnetic induction-based shock detection approach.

It is to be appreciated that the processor(s) 200 may detect that an electrical shock has been delivered via the electrodes 104 in other ways, such as by detecting the presence of an electromagnetic field generated by the delivery of the electrical shock. For example, the detection circuit 212 may include a Hall effect sensor(s) that is configured to detect an electromagnetic field generated by the delivery of the electrical shock. Another example shock detection approach is to include a physical wire tap into the electrode leads 112. This is sometimes referred to herein as a conductive-based shock detection approach. The detection circuit 212, in some examples, may be configured to detect a front end and a trailing end of an electrical pulse corresponding to the electrical shock in order to detect when an electrical shock has been delivered. In yet another example, the detection circuit 212 may include a capacitor that is charged by a portion of the electrical current associated with the electrical shock, and a detected change in the charge level of the capacitor may be used as a proxy to detect when an electrical shock has been delivered. In other examples, detection circuit 212 may include a resistor, and a detected change potential (e.g., voltage) associated with the resistor may be used as a proxy to detect when an electrical shock has been delivered. In some examples, the detection circuit 212 may include a resistor or a coil, and electrical current may flow through the resistor or the coil when an electrical shock is delivered. In some examples, a microcontroller may be used to reprogram a radio frequency identification (RFID) component by the pulses sensed on the resistor or the coil.

In some examples, the electrodes 104 may include a shock button 216, which may be disposed on the housing 120 of the electrode connector 114. The shock button 216 may be configured to be depressed by a user to cause a connected medical device 102, such as an external defibrillator, to deliver an electrical shock via the electrodes 104, and the detection circuit 212 may be configured to detect that the shock button 216 is depressed to determine that an electrical shock has been delivered via the electrodes 104. In some examples, actuation of the shock button 216 is detected using a mechanical switch, a proximity sensor (e.g., a capacitive sensor), a pressure sensor (e.g., a force-sensing resistor (FSR)), or any other suitable detection mechanism, which may be part of the detection circuit 212 or a separate component.

In some examples, the processor(s) 200 may execute the shock counter 204 to detect discrete electrical shocks that are administered in very quick succession, such as when two sequential electrical shocks are delivered within milliseconds of each other. Accordingly, the processor(s) 200 may execute the shock counter 204 to count two electrical shocks even when the interval between sequential shocks is very short, such as an interval of a few (e.g., 3, 5, 10, etc.) milliseconds.

FIG. 2 illustrates that the set of electrodes 104 may include additional electronic component(s) 218 in addition to those described herein, such as various integrated circuits (ICs), sensors, controllers, analog circuits, computer chips, or the like. Functional operation of the electrodes 104 may depend, at least in part, on these additional electronic components 218, and, as such, the condition of the additional electronic components 218 may be assessed periodically, such as by the processor 200 running diagnostic tests to ensure that the additional electronic components 218 are operational.

In some examples, the output device(s) 106 may include a display(s) 220, a light emitting element(s) 222 (e.g., a light emitting diode(s) (LED(s))), an electrochromic material(s) 224, a speaker(s) 226, a haptic actuator(s) 228, a transmitter(s) 230 (e.g., a transceiver, such as a wireless radio, antenna, or the like). The usability indication 108 may be output via any of these example output devices 106, and possibly multiple ones of the example output devices 106 simultaneously or at different times. In an example, the display(s) 220 is configured to output the usability indication 108 in the form of a visual indication, such as a color, text, graphics, animations, video, or the like. For example, the processor(s) 200 may execute instructions that cause the display to output a first color (e.g., red) indicating that the electrodes 104 should be replaced, and/or a second color (e.g., green) indicative of the electrodes 104 being usable. As another example, the display 220 is configured to output text (e.g., a number of shocks delivered, a cumulative amount of energy associated with the delivered electrical shocks, a life remaining based on an expiration date of the electrodes 104, a notification or a warning that the electrodes 104 should be replaced, etc.).

In some examples, the light emitting element(s) 222 is configured to output the usability indication 108 in the form of a visual indication, such as a color of light, a frequency of light pulses (e.g., blink frequency), an intensity of light (e.g., bright light, dim light, etc.), or the like. For example, a red light and/or a flashing light is an example of a usability indication 108 indicating that the electrodes 104 should be replaced. In an example, the light emitting element(s) 222 may be disposed at the electrode connector 114 (e.g., on the housing 120 or within a translucent housing 120).

In some examples, the electrochromic material(s) 224 is configured to output the usability indication 108 in the form of a color. Electrochromic materials, also known as chromophores, affect the optical color or opacity of a surface when a voltage is applied. Examples of electrochromic materials 224 include metal oxides, tungsten oxide, molybdenum, titanium and niobium oxides, or polypyrrole. In an example, the electrochromic material(s) 224 may be disposed at one or both of the electrodes 110, such as on the back of the electrode(s) 110, at one or both of the electrode leads 112, and/or at the electrode connector 114 (e.g., on the housing 120 or within a translucent housing 120).

In some examples, the speaker(s) 226 is configured to output the usability indication 108 in the form of an audio indication, such as a voice prompt, a sound, or the like. In some examples, the haptic actuator(s) 228 is configured to output the usability indication 108 in the form of a haptic indication, such as a vibration of the electrode connector 114, which may be audible as well. In some examples, the transmitter(s) 230 is configured to transmit the usability indication 108 to an external device for display of the usability indication 108 on a display of the external device and/or for output of the usability indication 108 via a speaker of the external device. In this example, the external device may be the medical device 102, a mobile phone, a digital tablet, or the like.

In an example where the usability indication 108 is provided in the form of a color (e.g., a color output via the display(s) 220, via the light emitting element(s) 222, and/or the electrochromic material(s) 224), a first color (e.g., red) indicates that the electrodes 104 should be replaced or discarded. In some examples, a second color (e.g., green) is indicative of the electrodes 104 being usable, which can provide assurance for a user of the electrodes 104 that they indeed are usable. In some examples, a color gradient can be used to indicate how close the electrodes 104 are to a recommendation to replace the electrodes 104. For example, a yellow color may be output by an output device(s) 106 if the electrodes 104 are close to expiration, close to a shock limit, or the like, meaning that they should soon be replaced once the electrodes 104 become expired and/or reach their shock limit. In an example where the usability indication 108 is based on the number of shocks delivered, the output device(s) 106 may output a green color when the electrodes 104 are removed from their sealed pouch, and as electrical shocks are delivered via the electrodes 104 and the shock count 210 increments to a halfway point (e.g., a number that is half of the maximum number of shocks for which the electrodes 104 are rated), the color may change to yellow, and once the shock count 210 reaches the threshold (e.g., the maximum number of shocks for which the electrodes 104 are rated), the color may change to red, indicating that the electrodes 104 should be replaced. Accordingly, a user may notice the yellow color and may start making preparations to replace the electrodes 104, such as by obtaining a replacement set of electrodes 104 so that the replacement set is at the ready for use, if needed.

Instead of, or in addition to, using colors for the usability indication 108, as described herein, other indicia, such as shapes, may be used to indicate whether the electrodes 104 are usable or whether they should be replaced, which may assist color blind users. For example, a first shape (e.g., a triangle) output by an output device(s) 106 (e.g., the display(s) 220, an array of the light emitting element(s) 222, and/or the electrochromic material(s) 224) of the set of electrodes 104 may indicate that the electrodes 104 should be replaced or discarded. In some examples, a second shape (e.g., a circle) output by the output device(s) 106 may be indicative of the electrodes 104 being usable. In some examples, a third shape (e.g., a square) output by the output device(s) 106 may correspond to the "yellow" color mentioned above to indicate that the electrodes 104 are still usable, but may need to be replaced soon.

The set of electrodes 104 may further include a power source 232, such as a battery(ies), a solar cell(s), or the like. The power source 232 can provide power to the various electronic components of the electrodes 104 so that a usability indication can be output even when the electrodes 104 are disconnected from a medical device 102. In some examples, the power source 232 is controllable to place the electrodes 104 into a sleep state when they are not in use, which may conserve power. In these examples, the electrodes 104 may "wake up" in response to any suitable trigger, and, in response, the power source 232 may supply power to an electronic component(s) so that a usability indication 108 is output. A user may provide user input to wake up the electrodes 104 (e.g., by touching a touch-sensitive display 220), or the electrodes 104 may wake up based on a sensor (e.g., an ambient light sensor, an accelerometer, etc.) sensing a state change.

It is to be appreciated that the processor(s) 200 may execute instructions stored in memory 202 in order to cause the usability indication 108 to be output via an output device(s) 106 of the electrodes 104. For example, the condition assessment module 208 may represent instructions executable by the processor(s) 200 to determine any suitable condition(s) that may dictate whether a usability indication 108 is to be output and/or which type of usability indication 108 is to be output, if multiple types of usability indications 108 are available. In some examples, the processor(s) 200 may cause the usability indication 108 to be output via an output device 106 in a persistent manner (e.g., the output device 106 may persistently output a usability indication 108 that is updated by the processor(s) 200). Various examples of usability indications 108 are described below with reference to the following figures.

Figure 3A:
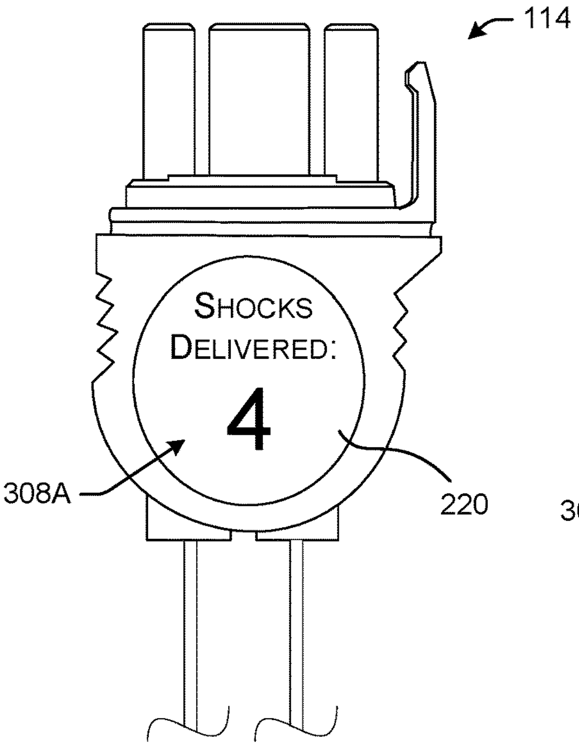
FIG. 3A illustrates an example usability indication output by an output device disposed at an electrode connector, according to the techniques described herein.
Figure 3B:
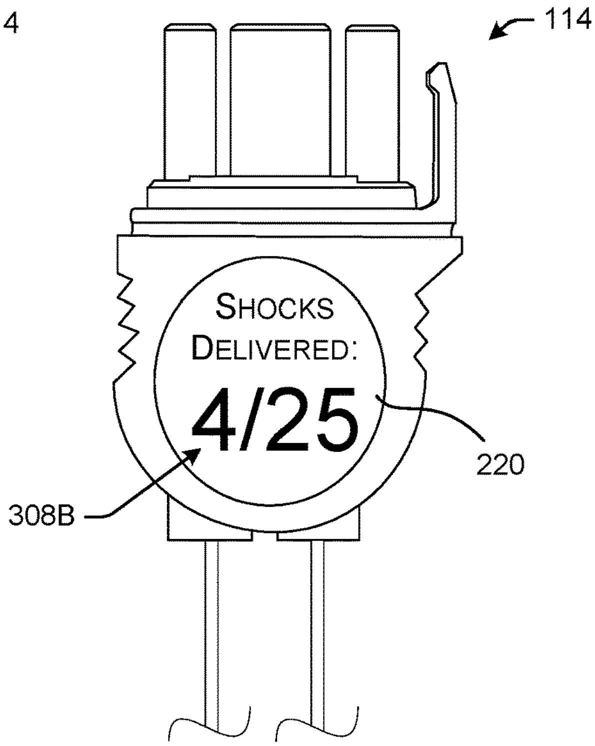
FIG. 3B illustrates an example usability indication output by an output device disposed at an electrode connector, according to the techniques described herein.

FIG. 3A illustrates an example usability indication 308A output by an output device 106 disposed at an electrode connector 114, according to the techniques described herein. The example output device 106 in FIG. 3A is a display 220 of the electrode connector 114. For example, the display 220 may be disposed on the housing 120 of the electrode connector 220. The display 220 may be any suitable type of display, such as a liquid crystal display (LCD), an organic light emitting diode (OLED) display, an electronic paper (e-paper) display, or any other suitable type of display. The usability indication 308A depicted in FIG. 3A is an example of the usability indication 108 described herein. In this example, the usability indication 308A is a number of electrical shocks delivered via the electrodes 104, which is based on the shock count 210 stored in the memory 202 of the electrodes 104. In other words, the example usability indication 308A is based on the number of electrical shocks delivered via the set of electrodes 104. In the example of FIG. 3A, the usability indication 308A indicates that four electrical shocks have been delivered via the electrodes 104. A user of the electrodes, such as a EMT, may know the shock limit (or maximum number of shocks) for which the electrodes 104 are rated, and as such the usability indication 308A may indicate, to the user, that the electrodes 104 are usable because they have not reached their shock limit yet. To assist less experienced users, and/or to provide more information generally, FIG. 3B illustrates an example usability indication 308B that displays the number of electrical shocks delivered via the electrodes 104 as a fraction to indicate the number of electrical shock remaining until a threshold (e.g., maximum number of shocks) is reached. In the example of FIG. 3B, the usability indication 308B indicates that four out of twenty five electrical shocks have been delivered, thereby indicating that twenty one electrical shocks can be delivered before a threshold (e.g., maximum number of shocks) is reached. Additionally, or alternatively, a percentage of allowed electrical shocks delivered and/or a percentage of allowed electrical shocks remaining may be output (e.g., via the display 220). In some examples, the usability indication 308A, 308B may be color-coded to help the user better understand the usability of the electrodes. For example, the usability indication 308A, 308B shown in FIG. 3A, 3B may be presented in green-colored text to indicate that the electrodes 104 are usable, and once the shock limit is reached, the number of electrical shocks displayed on the display 220 may be presented in red-colored text. All references to color can include a counterpart shape or associated designation for interpretation by color blind users. It is to be appreciated that, as the shock count 210 is incremented, the usability indication 308A, 308B output via the display 220 may be updated with the current shock count 210. In this way, a user can readily determine the number of shocks that have been delivered via the electrodes 104, without having to rely on someone else to verbally relay the same information, or manually track the number of shocks delivered. In some examples, the usability indication 308A, 308B may represent a number of electrical shocks delivered at a particular energy level, and/or by a particular defibrillator, and the user may be able to toggle between user interfaces, such as by swiping left, right, up, or down on the display 220 to reveal other shock counts associated with other energy levels and/or other defibrillators, as described herein.

Figure 4:
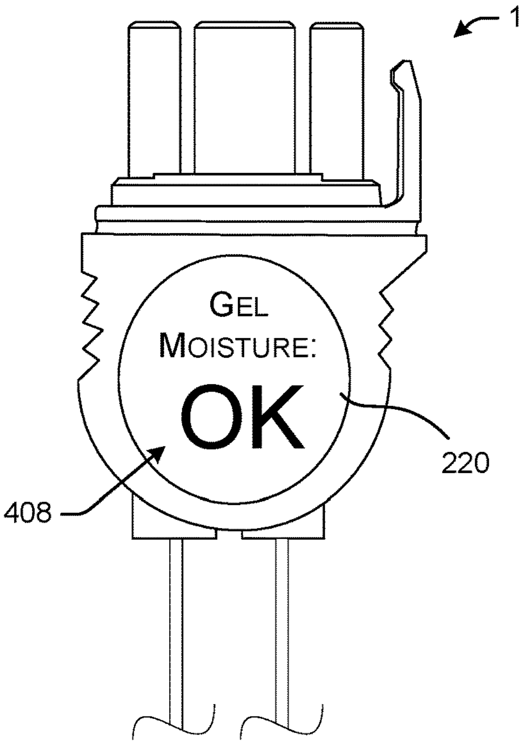
FIG. 4 illustrates an example usability indication output by an output device disposed at an electrode connector, according to the techniques described herein.

FIG. 4 illustrates an example usability indication 408 output by an output device 106 disposed at an electrode connector 114, according to the techniques described herein. The example output device 106 in FIG. 4 is a display 220 of the electrode connector 114, which may be similar to the display 220 described with reference to FIG. 3A, above. The usability indication 408 depicted in FIG. 4 is an example of the usability indication 108 described herein. In this example, the usability indication 408 is a "gel moisture" indication, which is based on a moisture of the gel disposed on the electrode pad(s) 110. For example, a gel integrity sensor may be configured to detect a moisture of the gel, and/or an electrical conductivity of the gel, and based on these sensed parameters, a condition of the gel may be determined by the processor(s) 200 receiving the sensed parameter(s) from the gel integrity sensor. Accordingly, the example usability indication 408 may indicate to a user that the electrodes are usable because a condition (e.g., moisture) of the gel is "OK" (e.g., at or above a threshold moisture content). In some examples, the usability indication 408 may be color-coded to help the user better understand the usability of the electrodes. For example, the usability indication 408 shown in FIG. 4 may be presented in green-colored text to indicate that the electrodes 104 are usable, and once the condition (e.g., moisture) of the gel is not "OK" (e.g., at or below a threshold moisture content), the text displayed on the display 220 may be presented in red-colored text. When text is color-coded, different fonts or styles (e.g. underlined, italics) maybe incorporated for use by color blind users.

Figure 5:
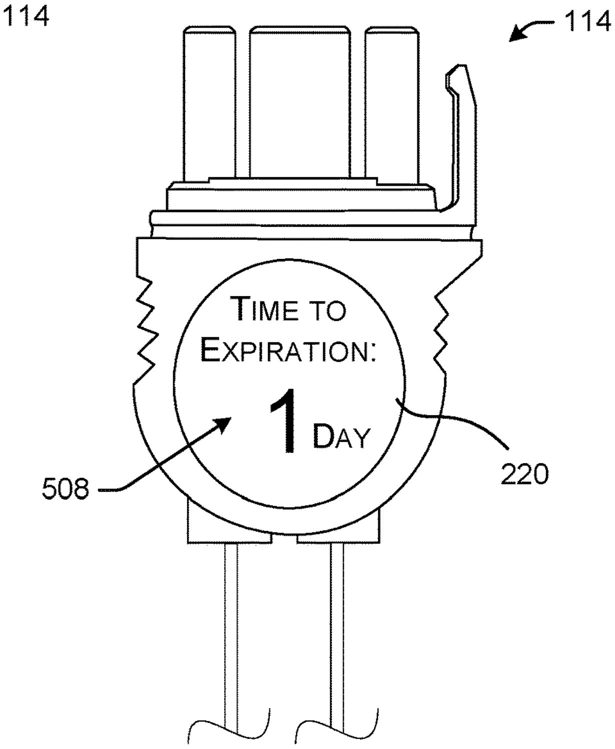
FIG. 5 illustrates an example usability indication output by an output device disposed at an electrode connector, according to the techniques described herein.

FIG. 5 illustrates an example usability indication 508 output by an output device 106 disposed at an electrode connector 114, according to the techniques described herein. The example output device 106 in FIG. 5 is a display 220 of the electrode connector 114, which may be similar to the display 220 described with reference to FIG. 3A, above. The usability indication 508 depicted in FIG. 5 is an example of the usability indication 108 described herein. In this example, the usability indication 508 is a "time to expiration" of the electrodes 104, which is based on a date(s) 234 stored in the memory 202 of the electrodes 104. For example, the memory 202 may store a date(s) 234, such as a date on which the electrodes 104 were manufactured, an expiration date, or the like. The processor(s) 200 may execute instructions (e.g., the condition assessment module 208) to determine the current date and may compare the current date to the date(s) 234 stored in the memory 202 to determine an expired or unexpired condition of the electrodes 104. The current date may be determined by a clock, or by using a communications interface to access a network (e.g., the Internet) to determine the current date. Accordingly, the example usability indication 508 is based on the stored date(s) 234 and the current date determined by the processor(s) 200. For example, if the current date precedes an expiration date 234 stored in memory 202 by one day, the processor(s) 200 may cause the usability indication 508 to be output via the display 200 (e.g., "Time To Expiration: 1 Day"). This type of usability indication 508 may be referred to as a remaining life of the electrodes 508, and it may indicate to a user that the electrodes are usable because they have some remaining life. If the current date coincides with, or is past, an expiration date 234 stored in memory 202, the usability indication 508 may be updated to indicate "zero days" or "expired," which may inform a user that the electrodes 104 should be replaced. In some examples, the usability indication 508 may be color-coded to help the user better understand the usability of the electrodes. For example, the usability indication 508 shown in FIG. 5 may be presented in green-colored text to indicate that the electrodes 104 are usable, and once the expiration date is reached, the text displayed on the display 220 may be presented in red-colored text. When text is color-coded, different fonts or styles (e.g. underlined, italics) maybe incorporated for use by color blind users.

Figure 6:
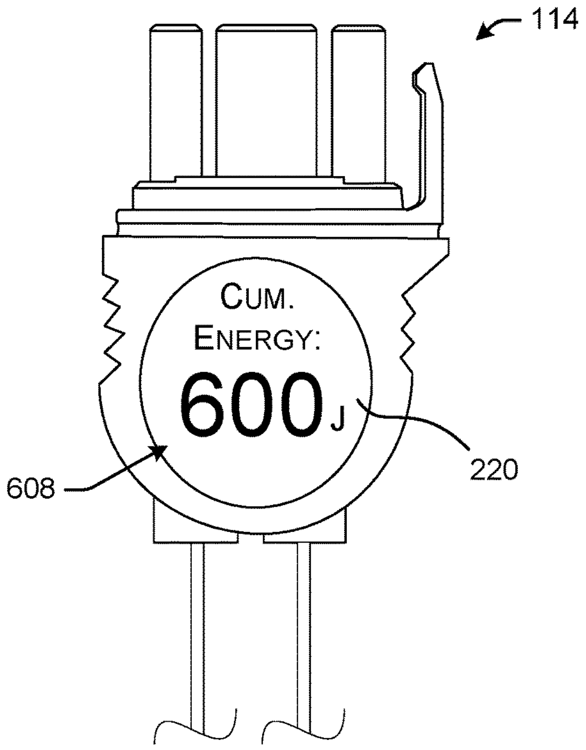
FIG. 6 illustrates an example usability indication output by an output device disposed at an electrode connector, according to the techniques described herein.

FIG. 6 illustrates an example usability indication 608 output by an output device 106 disposed at an electrode connector 114, according to the techniques described herein. The example output device 106 in FIG. 6 is a display 220 of the electrode connector 114, which may be similar to the display 220 described with reference to FIG. 3A, above. The usability indication 608 depicted in FIG. 6 is an example of the usability indication 108 described herein. In this example, the usability indication 608 is a cumulative amount of energy delivered via electrical shocks delivered via the electrodes 104, which is based on cumulative energy 236 data stored in the memory 202 of the electrodes 104. In other words, the example usability indication 608 is based on the cumulative amount of energy delivered via electrical shocks delivered via the set of electrodes 104. With brief reference to FIG. 2, the energy meter 206 may be executed by the processor(s) 200 to detect the amount of energy (e.g., measured in J) at which an electrical shock is delivered, and to track the cumulative energy delivered over a series of electrical shocks and store the cumulative energy 236 in the memory 202 of the electrodes 104. In the example of FIG. 6, the usability indication 608 indicates that 600 J of energy have been delivered via an electrical shock(s) delivered via the electrodes 104. A user of the electrodes, such as an EMT, may know an energy limit (or maximum shock energy) for which the electrodes 104 are rated, and as such the usability indication 608 may indicate, to the user, that the electrodes 104 are usable because they have not reached their energy limit yet. In some examples, the usability indication 608 may be color-coded to help the user better understand the usability of the electrodes. For example, the usability indication 608 shown in FIG. 6 may be presented in green-colored text to indicate that the electrodes 104 are usable, and once the energy limit is reached, the cumulative amount of energy displayed on the display 220 may be presented in red-colored text. It is to be appreciated that, as the cumulative energy 236 increases with additional shocks delivered, the usability indication 608 output via the display 220 may be updated with the current cumulative energy 236. In this way, a user can readily determine the cumulative energy that has been delivered via the electrodes 104.

It is to be appreciated that a user may be able to navigate between the information depicted in FIGS. 3A, 3B, 4, 5, and/or 6, such as by swiping left or right (or up or down) on a touch-sensitive display 220, depressing a button, or the like. That is a user may be able to choose what is displayed on the display 220 in instances where the display 220 is not big enough to present all of the available information. Furthermore, it is to be appreciated that the information depicted in FIGS. 3A, 3B, 4, 5, and/or 6 is exemplary and other information, as described herein, may be displayed on the display 220.

Figure 7:
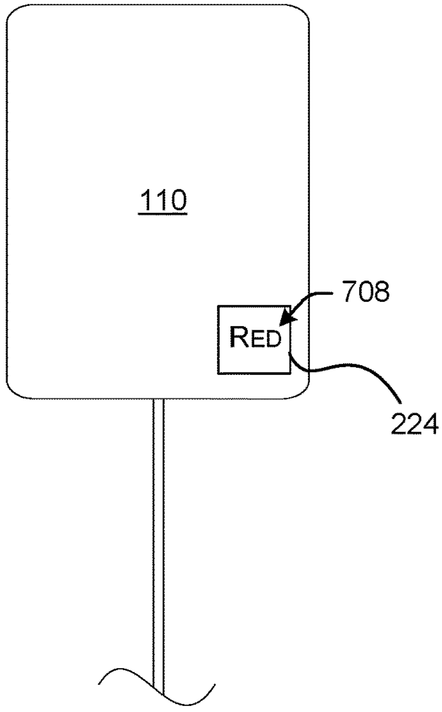
FIG. 7 illustrates an example usability indication output by an output device disposed at an electrode, according to the techniques described herein.

FIG. 7 illustrates an example usability indication 708 output by an output device 106 disposed at an electrode 110, according to the techniques described herein. The example output device 106 in FIG. 7 is an electrochromic material 224 that is disposed on, or is part of, the electrode 110, such as the material on the back side of the electrode 110. The usability indication 708 depicted in FIG. 7 is an example of the usability indication 108 described herein. In this example, the usability indication 708 is a visual indication, and particularly a color (e.g., a red-colored material). The electrochromic material 224 may be configured to change between multiple different colors, such as red and green. In this way, the a first color (e.g., red) may indicate that the electrodes 104 should be replace, and/or a second color (e.g., green) may indicate that the electrodes 104 are usable. Furthermore, the example usability indication 708 can be based on any suitable condition(s) of the electrodes 104 described herein, such as a number of electrical shocks delivered, a cumulative amount of energy delivered via the electrical shocks, an expired or unexpired condition of the electrodes 104, a condition of the gel disposed on the electrodes 104, a condition of an electronic component of the electrodes 104, or the like.

Figure 8:
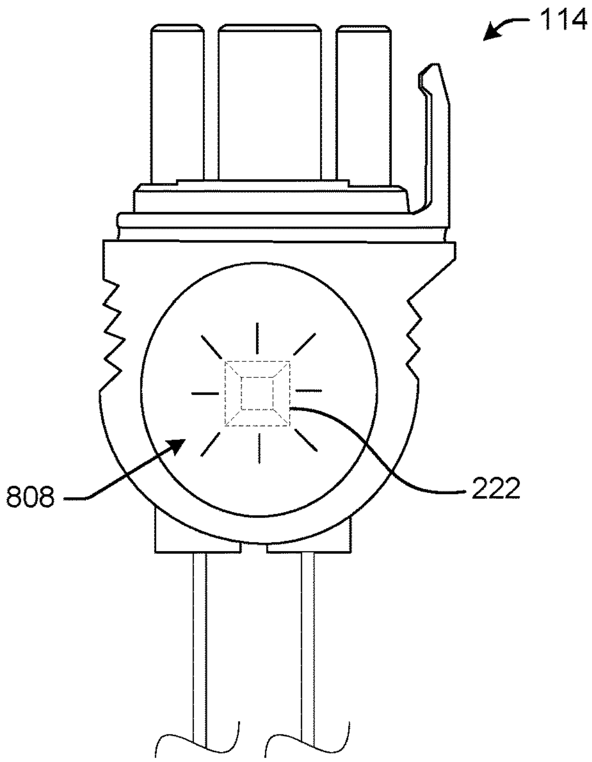
FIG. 8 illustrates an example usability indication output by an output device disposed at an electrode connector, according to the techniques described herein.

FIG. 8 illustrates an example usability indication 808 output by an output device 106 disposed at an electrode connector 114, according to the techniques described herein. The example output device 106 in FIG. 8 is a light emitting element 222, such as an LED. The light emitting element 222 may be disposed on the housing 120 of the electrode connector 114 or within a translucent housing 120 of the electrode connector 114. The usability indication 808 depicted in FIG. 8 is an example of the usability indication 108 described herein. In this example, the usability indication 808 is a visual indication, and particularly light, which may be output as a particular color, and/or as a flashing light (e.g., light pulses at any suitable blink frequency), and/or at any suitable intensity. The light emitting element 222 may be configured to change between multiple different colors, such as red and green, and/or change between an off state, an on state, a flashing state, or the like. In some examples, the light emitting element 222 may output light of any color and/or intensity to indicate that the electrodes 104 should be replaced. In other examples, a particular color (e.g., red), intensity (e.g., bright), and/or flashing state may indicate that the electrodes 104 should be replaced. In some examples, a particular color (e.g., green) may indicate that the electrodes 104 are usable. Furthermore, the example usability indication 808 can be based on any suitable condition(s) of the electrodes 104 described herein, such as a number of electrical shocks delivered, a cumulative amount of energy delivered via the electrical shocks, an expired or unexpired condition of the electrodes 104, a condition of the gel disposed on the electrodes 104, a condition of an electronic component of the electrodes 104, or the like.

Figure 9:
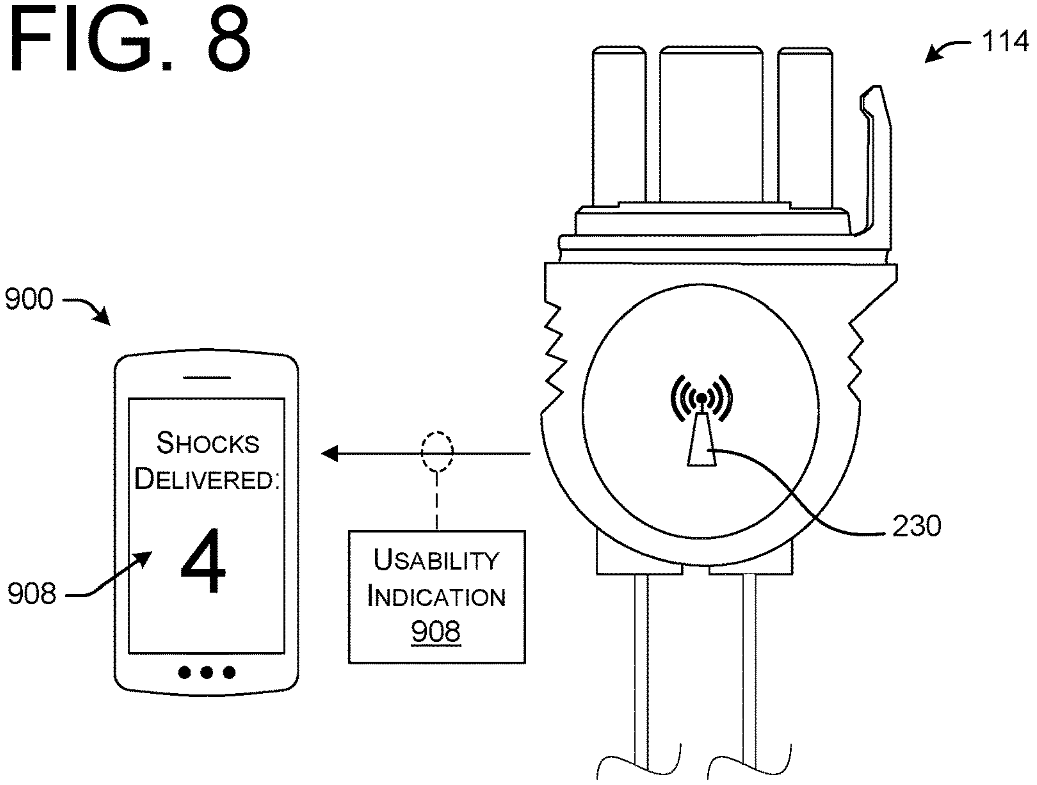
FIG. 9 illustrates an example usability indication output by an output device disposed at an electrode connector, and an external device that outputs the usability indication on a display of the external device, according to the techniques described herein.

FIG. 9 illustrates an example usability indication 908 output by an output device 106 disposed at an electrode connector 114, according to the techniques described herein. The example output device 106 in FIG. 9 is a transmitter 230, such as a wireless radio (e.g., a Bluetooth® radio, a WiFi radio, etc.). The transmitter 230 may be disposed within the housing 120 of the electrode connector 114. The usability indication 908 depicted in FIG. 9 is an example of the usability indication 108 described herein. In this example, the usability indication 908 is transmitted (e.g., wirelessly) by the transmitter to an external device 900 for display of the usability indication 908 on a display of the external device 900. In this example, the external device 900 is depicted as a mobile phone, but it is to be appreciated that the external device 900 can be any suitable device, including the medical device 102 depicted in FIG. 1. Furthermore, the usability indication 908 is displayed as a number of electrical shocks delivered via the electrodes 104, which is based on the shock count 210 stored in the memory 202 of the electrodes 104. In other words, the example usability indication 908 is based on the number of electrical shocks delivered via the set of electrodes 104. In the example of FIG. 9, the usability indication 908 indicates that four electrical shocks have been delivered via the electrodes 104, which informs a user that the electrodes 104 have not yet reached their shock limit, if the shock limit is greater than four shocks. In some examples, a client application may be downloaded on the external device 900 in order to receive a usability indication 908 from the transmitter 230 of the electrodes 104 and display the usability indication 908 via a user interface of the client application executing on the external device 900.

The processes described herein represent sequences of operations that can be implemented in hardware, software, or a combination thereof. In the context of software, the blocks represent computer-executable instructions stored on one or more computer-readable storage media that, when executed by a processor(s), perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes. In some examples, an operation(s) of the process may be omitted entirely. Moreover, the processes described herein can be combined in whole or in part with each other or with other processes.

Figure 10:
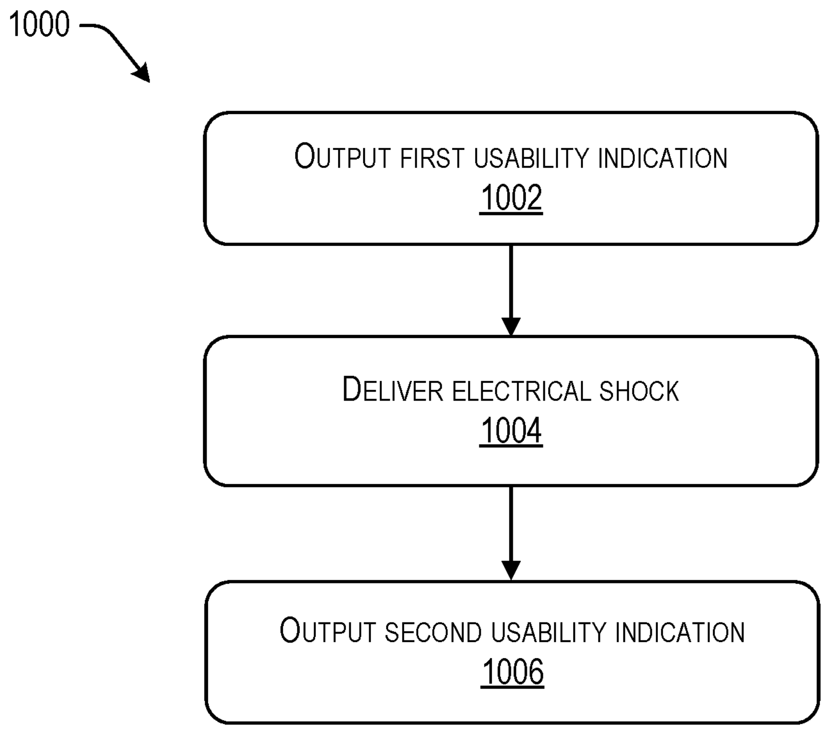
FIG. 10 illustrates an example process is an example process implemented by a set of electrodes for outputting a usability indication based on an electrical shock(s) delivered via the electrodes, according to the techniques described herein.

FIG. 10 illustrates an example process 1000 implemented by a set of electrodes 104 for outputting a usability indication based on an electrical shock(s) delivered via the electrodes 104, according to the techniques described herein. For discussion purposes, the process 1000 is described with reference to the previous figures.

At 1002, an output device(s) 106 of a set of electrodes 104 may output, at a first time, a first usability indication 108 indicating that the set of electrodes 108 are usable. The output device 106 may be any suitable output device, such as any of the example output devices 106 described herein. In some examples, the output device 106 is a display 220, such as a display 220 disposed at an electrode connector 114 of the set of electrodes 104, and the first usability indication 108 may be displayed via the display 220 at block 1002. In some examples, the output device(s) 106 is a light emitting element(s) 222, an electrochromic material(s) 224, a speaker(s) 226, a haptic actuator(s) 228, and/or a transmitter(s) 230. In the example of a transmitter 230, the transmitter 230 may transmit the first usability indication

108 to an external device 900 for output (e.g., display) of the first usability indication 108 via an output device (e.g., a display) of the external device 900.

At 1004, the set of electrodes 104 may deliver, at a second time after the first time, via a first electrode 110(1) and a second electrode 110(2) of the set of electrodes 104, an electrical shock to a patient. The first electrode 110(1) and the second electrode 110(2) are attached to an external surface of the patient during the delivering of the electrical shock at block 1004. The set of electrodes 104 may be coupled to a medical device 102, such as an external defibrillator, which is the source of the electrical shock, as described herein.

At 1006, the output device(s) 106 of the set of electrodes 104 may output, at a third time after the first time, a second usability indication 108 indicating that the set of electrodes 104 are unusable. An indication that the electrodes 104 are "unusable" at block 1006 does not necessarily mean that the electrodes 104 cannot be used for their intended purpose (e.g., to deliver an electrical shock(s)). Rather, "unusable" in this context means that the electrodes should be replaced (or discarded) to mitigate the risk of compromising the care of a patient. For example, at block 1002, the shock count 210 may have been one shock less than a shock limit, and after delivery of the electrical shock at block 1004, the shock count 210 may have been incremented to a number of shocks that equals the shock limit for the electrodes 104. Accordingly, the second usability indication 108 may be output based on assessing this condition of the electrodes 104. In another example, the second usability indication 108 may be output as the number of shocks that have been delivered via the electrodes 104, possibly without assessing whether a shock limit has been reached. In yet another example, the second usability indication 108 may be output as a cumulative amount of energy delivered via the electrical shocks delivered via the electrodes 104.

Figure 11:
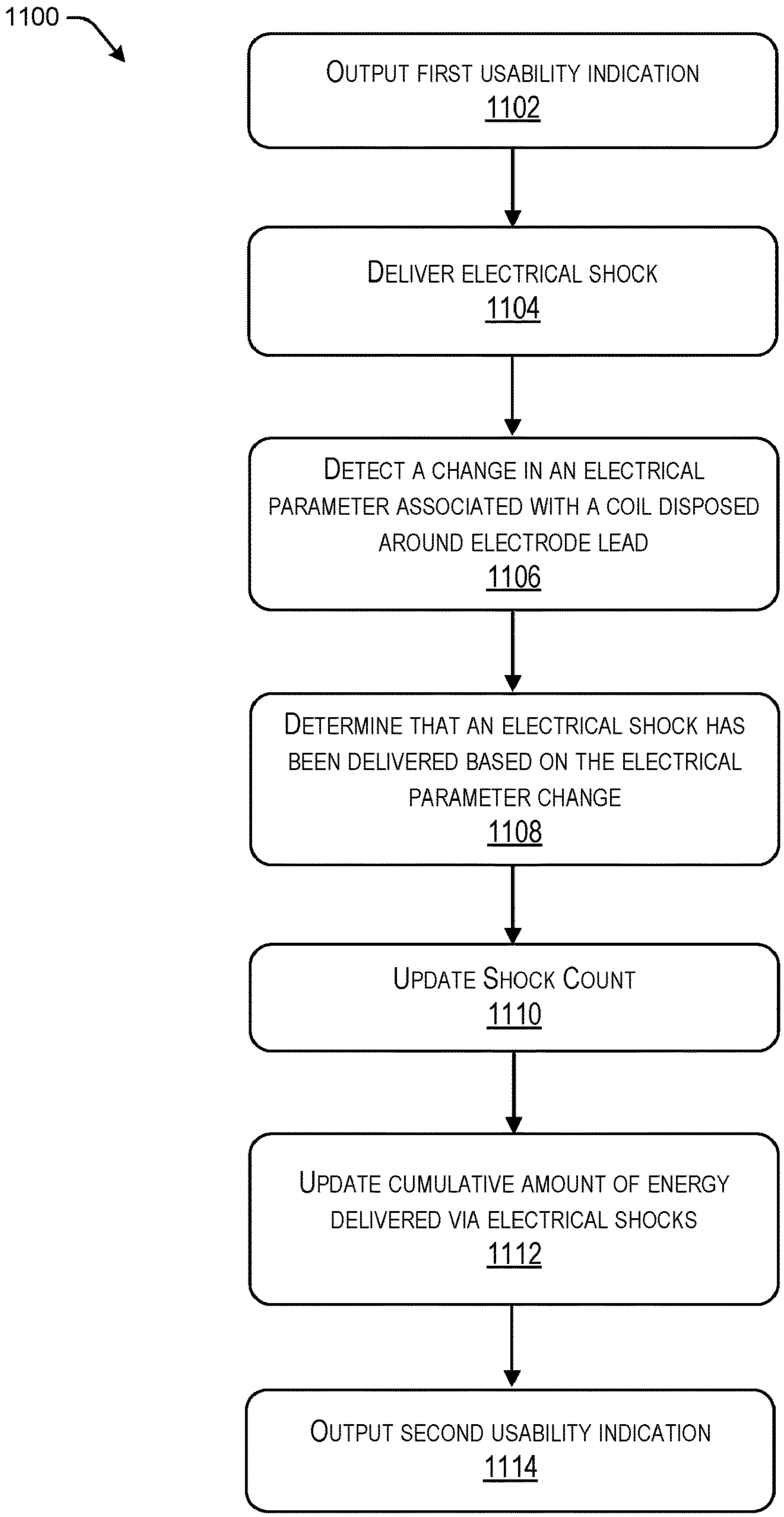
FIG. 11 illustrates an example process is an example process implemented by a set of electrodes for outputting a usability indication based on an electrical shock(s) delivered via the electrodes, according to the techniques described herein

FIG. 11 illustrates an example process 1100 implemented by a set of electrodes 104 for outputting a usability indication based on an electrical shock(s) delivered via the electrodes 104, according to the techniques described herein. For discussion purposes, the process 1100 is described with reference to the previous figures.

At 1102, an output device(s) 106 of a set of electrodes 104 may output, at a first time, a first usability indication 108 indicating that the set of electrodes 108 are usable. The output device 106 may be any suitable output device, such as any of the example output devices 106 described herein. In some examples, the output device 106 is a display 220, such as a display 220 disposed at an electrode connector 114 of the set of electrodes 104, and the first usability indication 108 may be displayed via the display 220 at block 1102. In some examples, the output device(s) 106 is a light emitting element(s) 222, an electrochromic material(s) 224, a speaker(s) 226, a haptic actuator(s) 228, and/or a transmitter(s) 230. In the example of a transmitter 230, the transmitter 230 may transmit the first usability indication 108 to an external device 900 for output (e.g., display) of the first usability indication 108 via an output device (e.g., a display) of the external device 900.

At 1104, the set of electrodes 104 may deliver, at a second time after the first time, via a first electrode 110(1) and a second electrode 110(2) of the set of electrodes 104, an electrical shock to a patient. The first electrode 110(1) and the second electrode 110(2) are attached to an external surface of the patient during the delivering of the electrical shock at block 1104. The set of electrodes 104 may be coupled to a medical device 102, such as an external defibrillator, which is the source of the electrical shock, as described herein.

At 1106, a detection circuit 212 of the set of electrodes 104 may detect a change in an electrical parameter(s) (e.g., electrical current, voltage, etc.) associated with a coil 214 disposed around an electrode lead 112 of the set of electrodes 104.

At 1108, a processor(s) 200 of the set of electrodes 104 may determine that the electrical shock has been delivered based on the change in the electrical parameter(s) detected by the detection circuit 212.

At 1110, the processor(s) 200 may execute the shock counter 204 to update a shock count 210 in the memory 202 of the set of electrodes 104 based on determining that the electrical shock has been delivered. For example, the processor(s) 200 may execute the shock counter 204 to count a number of electrical shocks delivered to the patient via the first electrode 110(1) and the second electrode 110(2), and the processor(s) 200 may store, in the memory 202 (e.g., non-volatile memory) of the set of electrodes 104, the number of the electrical shocks delivered (e.g., the shock count 210).

At 1112, a processor(s) 200 of the set of electrodes 104 may update a cumulative amount of energy 236 in the memory 202 of the set of electrodes 104 based on determining that the electrical shock has been delivered and metering the energy at which the shock was delivered (e.g., via the energy meter 206 executed by the processor(s) 200). For example, the processor(s) 200 may determine a cumulative amount of energy delivered via electrical shocks delivered to the patient via the first electrode 110(1) and the second electrode 110(2), and may store, in the memory 202 (e.g., non-volatile memory) of the set of electrodes 104, the cumulative amount of energy 236.

At 1114, the output device(s) 106 of the set of electrodes 104 may output, at a third time after the first time, a second usability indication 108 based on the number of the electrical shocks delivered and/or based on the cumulative amount of energy delivered. In some examples, this second usability indication 108 may indicate that the set of electrodes 104 are "unusable," or that the electrodes 104 should be replaced (or discarded). In some examples, the second usability indication 1114 is output as the number of shocks delivered and/or as the cumulative amount of energy delivered, as described herein. In some examples, the processor(s) 200 of the set of electrodes 104 may assess a condition(s) of the electrodes 104 relating to shock delivery, such as whether the number of shocks and/or the cumulative amount of energy is equal to or greater than a threshold.

Figure 12:
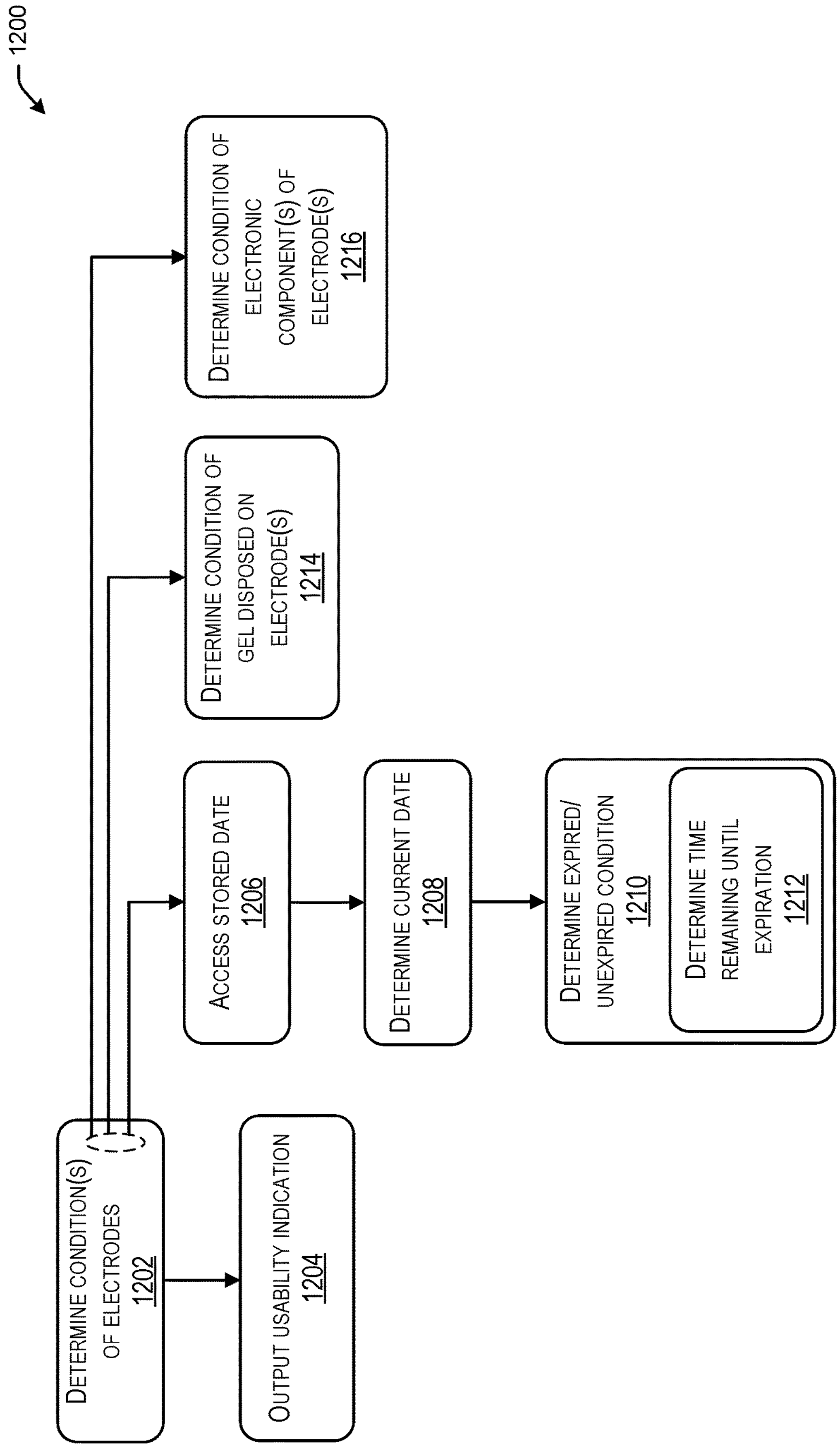
FIG. 12 illustrates an example process implemented by a set of electrodes for outputting a usability indication based on a condition(s) of the electrodes, according to the techniques described herein.

FIG. 12 illustrates an example process 1200 implemented by a set of electrodes 104 for outputting a usability indication based on a condition(s) of the electrodes 104, according to the techniques described herein. For discussion purposes, the process 1100 is described with reference to the previous figures.

At 1202, a processor(s) 200 of a set of electrodes 104 may determine a condition(s) of a set of electrodes 104. The condition(s) determined at block 1202 may indicate or dictate a usability of the electrodes 104. Example condition(s) that may be determined at block 1202 are discussed in more detail below.

At 1204, the output device(s) 106 of the set of electrodes 104 may output a usability indication 108 based on the condition(s) of the electrodes 104 determined at block 1202. In some examples, the condition of the electrodes 104 determined at block 1202 is the number of shocks delivered via the electrodes 104. In some examples, the condition of the electrodes 104 determined at block 1202 is the cumulative amount of energy delivered via electrical shocks delivered via the set of electrodes 104. In some examples, the usability indication 108 may be based on a condition that the number of shocks delivered via the set of electrodes 104 and/or the cumulative amount of energy delivered meets or exceeds a respective threshold (e.g., a threshold number of shock and/or a threshold cumulative amount of energy), as described herein.

Determining a condition(s) at 1202 may additionally or alternatively include other examples represented by sub-operations 1206-1212. For example, at 1206, the processor(s) 200 of the set of electrodes 104 may access, from the memory 202 (e.g., non-volatile memory) of a set of electrodes 104, a stored date 234 associated with the set of electrodes 104, which may be an expiration date, a date on which the electrodes 104 were manufactured, or the like.

At 1208, the processor(s) 200 of the set of electrodes 104 may determine a current date. This may be done using a clock of the set of electrodes 104, by accessing the Internet via a communications interface (e.g., the transmitter(s) 230, such as a WiFi radio), or the like.

At 1210, the processor(s) 200 of the set of electrodes 104 may determine an expired or unexpired condition of the set of electrodes. At 1212, determining the expired or unexpired condition may include determining, by the processor(s) 200, a time remaining until the set of electrodes 104 are expired based on the current date and the stored date 234. Accordingly, the usability indication 108 output at block 1204 may be based on a date(s) 234 stored in memory 202 of the electrodes 104 as compared to the current date, which may be indicative of an expired or an unexpired condition of the electrodes 104. In this example, the usability indication 108 may be output at block 1204 as the time remaining until the set of electrodes 104 are expired.

Determining a condition(s) at 1202 may include sub-operation 1214. For example, at 1214, the processor(s) 200 of the set of electrodes 104 may determine a condition of a gel disposed on an electrode(s) 110 of the set of electrodes 104. For example, a gel integrity sensor may be configured to detect a moisture of the gel, and/or an electrical conductivity of the gel, and based on these sensed parameters, a condition of the gel may be determined by the processor(s) 200 receiving the sensed parameter(s) from the gel integrity sensor. Accordingly, the usability indication 108 output at block 1204 may be based on the condition of the gel determined at block 1214.

Determining a condition(s) at 1202 may include sub-operation 1216. For example, at 1216, the processor(s) 200 of the set of electrodes 104 may determine a condition of an electronic component(s) (e.g., any of the components depicted in FIG. 2) of the set of electrodes 104. For example, the processor(s) 200 may be configured to run diagnostic tests to test the functioning of any particular electronic component and determine a condition thereof (e.g., functional, malfunctioning, etc.). Accordingly, the usability indication 108 output at block 1204 may be based on the condition of the electronic component(s) determined at block 1216.

EXAMPLE CLAUSES

1. A set of electrodes for an external defibrillator, the set of electrodes comprising: a first electrode configured to: couple to the external defibrillator via a first electrode lead; and attach to an external surface of a patient; and a second electrode configured to: couple to the external defibrillator via a second electrode lead; and attach to the external surface of the patient, wherein the first electrode and the second electrode are configured to deliver electrical shocks to the patient; and an output device configured to output a usability indication indicative of a usability of the set of electrodes.

2. The set of electrodes of clause 1, wherein the usability indication comprises a visual indication, an audio indication, or a haptic indication.

3. The set of electrodes of clause 2, wherein the visual indication comprises a color, a frequency of light pulses, or an intensity of light.

4. The set of electrodes of any one of clauses 1 to 3, further comprising: a processor configured to count a number of the electrical shocks delivered to the patient via the first electrode and the second electrode, wherein the usability indication is based on the number of the electrical shocks delivered.

5. The set of electrodes of clause 4, wherein: the output device comprises a display configured to display the usability indication; and the usability indication comprises the number of the electrical shocks delivered.

6. The set of electrodes of clause 4 or 5, further comprising non-volatile memory configured to store the number of the electrical shocks delivered.

7. The set of electrodes of any one of clauses 4 to 6, further comprising: a coil disposed around the first electrode lead; and a detection circuit configured to detect a change in electrical current associated with the coil, wherein the processor is configured to determine that an electrical shock has been delivered based on the change in the electrical current detected by the detection circuit.

8. The set of electrodes of any one of clauses 1 to 7, wherein: the first electrode lead has a first end coupled to the first electrode; the second electrode lead has a first end coupled to the second electrode; and the set of electrodes further comprises an electrode connector coupled to a second end of the first electrode lead and to a second end of the second electrode lead, the electrode connector being configured to couple to a port of the external defibrillator, wherein the output device is disposed at the electrode connector.

9. The set of electrodes of clause 8, wherein the output device comprises a display disposed on the electrode connector and configured to display the usability indication.

10. The set of electrodes of any one of clauses 1 to 7, wherein the output device is disposed at the first electrode.

11. A set of electrodes comprising: a first electrode configured to attach to an external surface of a patient; a second electrode configured to attach to the external surface of the patient; and an output device configured to output a usability indication indicative of a usability of the set of electrodes.

12. The set of electrodes of clause 11, wherein the usability indication comprises a visual indication.

13. The set of electrodes of clause 12, wherein the visual indication comprises a color.

14. The set of electrodes of any one of clauses 11 to 13, wherein: the first electrode is configured to couple to an external defibrillator via a first electrode lead; the second electrode is configured to couple to the external defibrillator via a second electrode lead; the first electrode and the second electrode are configured to deliver electrical shocks to the patient; the set of electrodes further comprises a processor configured to count a number of the electrical shocks delivered to the patient via the first electrode and the second electrode; and the usability indication is based on the number of the electrical shocks delivered.

15. The set of electrodes of clause 14, wherein: the output device comprises a display configured to display the usability indication; and the usability indication comprises the number of the electrical shocks delivered.

16. The set of electrodes of clause 14 or 15, further comprising non-volatile memory configured to store the number of the electrical shocks delivered.

17. The set of electrodes of any one of clauses 14 to 16, further comprising: a coil disposed around the first electrode lead; and a detection circuit configured to detect a change in electrical current associated with the coil, wherein the processor is configured to determine that an electrical shock has been delivered based on the change in the electrical current detected by the detection circuit.

18. The set of electrodes of any one of clauses 11 to 17, further comprising: a first electrode lead having a first end coupled to the first electrode; a second electrode lead having a first end coupled to the second electrode; and an electrode connector coupled to a second end of the first electrode lead and to a second end of the second electrode lead, the electrode connector being configured to couple to a port of an external device, wherein the output device is disposed at the electrode connector.

19. The set of electrodes of clause 18, wherein the output device comprises a display disposed on the electrode connector and configured to display the usability indication.

20. The set of electrodes of any one of clauses 11 to 19, further comprising: non-volatile memory storing a stored date associated with the set of electrodes; and a processor configured to determine a current date, wherein the usability indication is based on the stored date and the current date.

21. The set of electrodes of clause 20, wherein: the output device comprises a display configured to display the usability indication; and the usability indication comprises a time remaining until the set of electrodes are expired.

22. The set of electrodes of any one of clauses 11 to 21, wherein: the first electrode is configured to couple to an external defibrillator via a first electrode lead; the second electrode is configured to couple to the external defibrillator via a second electrode lead; the first electrode and the second electrode are configured to deliver electrical shocks to the patient; the set of electrodes further comprises a processor configured to determine a cumulative amount of energy delivered via the electrical shocks; and the usability indication is based on the cumulative amount of energy delivered.

23. The set of electrodes of clause 22, wherein: the output device comprises a display configured to display the usability indication; and the usability indication comprises the cumulative amount of energy delivered.

24. The set of electrodes of any one of clauses 11 to 23, further comprising a processor configured to determine a condition of a gel disposed on the first electrode, wherein the usability indication is based on the condition of the gel.

25. The set of electrodes of any one of clauses 11 to 24, further comprising: an electronic component; and a processor configured to determine a condition of the electronic component, wherein the usability indication is based on the condition of the electronic component.

26. The set of electrodes of any one of clauses 11 to 17 or 20 to 25, wherein the output device is disposed at the first electrode.

27. The set of electrodes of any one of clauses 11 to 26, wherein the output device comprises a transmitter configured to transmit the usability indication to an external device for display of the usability indication on a display of the external device.

28. A method comprising: outputting, at a first time, via an output device of a set of electrodes, a first usability indication indicating that the set of electrodes are usable; delivering, at a second time after the first time, via a first electrode and a second electrode of the set of electrodes, an electrical shock to a patient, wherein the first electrode and the second electrode are attached to an external surface of the patient during the delivering of the electrical shock; and outputting, at a third time after the first time, via the output device, a second usability indication indicating that the set of electrodes are unusable.

29. The method of clause 28, further comprising: counting, by a processor of the set of electrodes, a number of electrical shocks delivered to the patient via the first electrode and the second electrode, wherein the second usability indication is based on the number of the electrical shocks delivered.

30. The method of clause 29, further comprising storing, in non-volatile memory of the set of electrodes, the number of the electrical shocks delivered.

31. The method of any one of clauses 28 to 30, further comprising: detecting, by a detection circuit of the set of electrodes, a change in electrical current associated with a coil disposed around the first electrode lead; determining, by a processor of the set of electrodes, that the electrical shock has been delivered based on the change in the electrical current detected by the detection circuit.

32. The method of any one of clauses 28 to 31, further comprising: determining, by a processor of the set of electrodes, a cumulative amount of energy delivered via electrical shocks delivered to the patient via the first electrode and the second electrode, wherein the usability indication is based on the cumulative amount of energy delivered.

33. The method of any one of clauses 28 to 32, wherein: the output device comprises a display; and the outputting comprises displaying the second usability indication via the display.

34. The method of any one of clauses 28 to 32, wherein: the output device comprises a transmitter; and the outputting comprises transmitting the second usability indication via the transmitter to an external device for display of the usability indication on a display of the external device.

35. A method comprising: accessing, from non-volatile memory of a set of electrodes, a stored date associated with the set of electrodes; determining, by a processor of the set of electrodes, a current date; and outputting, via an output device of the set of electrodes, and based on the stored date and the current date, a usability indication indicative of a usability of the set of electrodes.

36. The method of clause 35, further comprising: determining, by the processor, a time remaining until the set of electrodes are expired based on the current date and the stored date; wherein the usability indication comprises the time remaining until the set of electrodes are expired.

37. The method of clause 35 or 36, wherein: the output device comprises a display; and the outputting comprises displaying the usability indication via the display.

38. The method of clause 35 or 36, wherein: the output device comprises a transmitter; and the outputting comprises transmitting the usability indication via the transmitter to an external device for display of the usability indication on a display of the external device.

39. A method comprising: determining, by a processor of a set of electrodes, a condition of a gel disposed on an electrode of the set of electrodes; and outputting, via an output device of the set of electrodes, and based on the condition of the gel, a usability indication indicative of a usability of the set of electrodes.

40. A method comprising: determining, by a processor of a set of electrodes, a condition of an electronic component of the set of electrodes; and outputting, via an output device of the set of electrodes, and based on the condition of the electronic component, a usability indication indicative of a usability of the set of electrodes.

41. A set of electrodes comprising: a first electrode coupled to a first end of a first electrode lead; a second electrode coupled to a first end of a second electrode lead; and an electrode connector coupled to a second end of the first electrode lead and to a second end of the second electrode lead, the electrode connector comprising; a housing, wherein a portion of the housing is configured to couple to a port of an external defibrillator; a processor disposed within the housing, the processor configured to count a number of electrical shocks delivered via the first electrode and the second electrode; and a display disposed on the housing, the display configured to display the number of the electrical shocks delivered.

42. A set of electrodes comprising: a first electrode configured to: attach to an external surface of a patient; and couple to an external defibrillator via a first electrode lead; a second electrode configured to: attach to the external surface of the patient; and couple to the external defibrillator via a second electrode lead; a coil disposed around the first electrode lead; a detection circuit configured to detect a change in electrical current associated with the coil; and a processor configured to: determine that an electrical shock has been delivered to the patient via the first electrode and the second electrode based on the change in the electrical current detected by the detection circuit; and count a number of electrical shocks delivered to the patient.

While the example clauses described above are described with respect to one particular implementation, it should be understood that, in the context of this document, the content of the example clauses can also be implemented via a method, device, system, computer-readable medium, and/or another implementation. Additionally, any one of examples 1-42 may be implemented alone or in combination with any other of the examples 1-42.

CONCLUSION

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; 18% of the stated value; 17% of the stated value; ±16% of the stated value; 15% of the stated value; 14% of the stated value; 13% of the stated value; 12% of the stated value; 11% of the stated value; 10% of the stated value; 9% of the stated value; ±8% of the stated value; 7% of the stated value; 6% of the stated value; 5% of the stated value; 4% of the stated value; 3% of the stated value; 2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All processes described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventors expect skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A set of electrodes for an external defibrillator, the set of electrodes comprising:

a first electrode configured to:

couple to the external defibrillator via a first electrode lead; and attach to an external surface of a patient;

a second electrode configured to:

couple to the external defibrillator via a second electrode lead; and attach to the external surface of the patient, wherein the first electrode and the second electrode are configured to deliver electrical shocks to the patient;

a processor configured to count a number of the electrical shocks delivered to the patient via the first electrode and the second electrode; and an output device configured to output a usability indication indicative of a usability of the set of electrodes, wherein the usability indication is based on the number of the electrical shocks delivered.

2. The set of electrodes of claim 1, further comprising:

a coil disposed around the first electrode lead; and a detection circuit configured to detect a change in electrical current associated with the coil, wherein the processor is configured to determine that an electrical shock has been delivered based on the change in the electrical current detected by the detection circuit.

3. The set of electrodes of claim 1, wherein:

the output device comprises a display configured to display the usability indication; and the usability indication comprises the number of the electrical shocks delivered.

4. The set of electrodes of claim 1, further comprising non-volatile memory configured to store the number of the electrical shocks delivered.

5. The set of electrodes of claim 1, further comprising:

a coil disposed around the first electrode lead; and a detection circuit configured to detect a change in electrical current associated with the coil, wherein the processor is configured to determine that an electrical shock has been delivered based on the change in the electrical current detected by the detection circuit.

6. A set of electrodes comprising:

a first electrode configured to:

couple to an external defibrillator via a first electrode lead; and attach to an external surface of a patient;

a second electrode configured to:

couple to the external defibrillator via a second electrode lead; and attach to the external surface of the patient, wherein the first electrode and the second electrode are configured to deliver electrical shocks to the patient;

a processor configured to determine a cumulative amount of energy delivered via the electrical shocks; and an output device configured to output a usability indication indicative of a usability of the set of electrodes, wherein the usability indication is based on the cumulative amount of the energy delivered.

7. The set of electrodes of claim 6, wherein the usability indication comprises a visual indication.

8. The set of electrodes of claim 6, wherein:

the processor is further configured to count a number of the electrical shocks delivered to the patient via the first electrode and the second electrode;

the output device is further configured to output a second usability indication indicative of the usability of the set of electrodes; and the second usability indication is based on the number of the electrical shocks delivered.

9. The set of electrodes of claim 8, wherein:

the output device comprises a display configured to display the second usability indication; and the second usability indication comprises the number of the electrical shocks delivered.

10. The set of electrodes of claim 8, further comprising non-volatile memory configured to store the number of the electrical shocks delivered.

11. The set of electrodes of claim 8, further comprising:

a coil disposed around the first electrode lead; and a detection circuit configured to detect a change in electrical current associated with the coil, wherein the processor is configured to determine that an electrical shock has been delivered based on the change in the electrical current detected by the detection circuit.

12. The set of electrodes of claim 6, wherein:

the first electrode lead has a first end coupled to the first electrode;

the second electrode lead has a first end coupled to the second electrode;

the set of electrodes further comprises an electrode connector coupled to a second end of the first electrode lead and to a second end of the second electrode lead, the electrode connector being configured to couple to a port of the external defibrillator; and the output device is disposed at the electrode connector.

13. The set of electrodes of claim 12, wherein the output device comprises a display disposed on the electrode connector and configured to display the usability indication.

14. The set of electrodes of claim 6, wherein the output device is disposed at the first electrode.

15. The set of electrodes of claim 6, wherein the output device comprises a transmitter configured to transmit the usability indication to an external device for display of the usability indication on a display of the external device.

16. A method comprising:

outputting, at a first time, via an output device of a set of electrodes, a first usability indication indicating that the set of electrodes are usable;

delivering, at a second time after the first time, via a first electrode and a second electrode of the set of electrodes, an electrical shock to a patient, wherein the first electrode and the second electrode are attached to an external surface of the patient during the delivering of the electrical shock;

counting, by a processor of the set of electrodes, a number of electrical shocks delivered to the patient via the first electrode and the second electrode; and outputting, at a third time after the first time, via the output device, a second usability indication indicating that the set of electrodes are unusable, wherein the second usability indication is based on the number of the electrical shocks delivered.

17. The method of claim 16, further comprising:

detecting, by a detection circuit of the set of electrodes, a change in electrical current associated with a coil disposed around an electrode lead coupled to the first electrode or the second electrode; and determining, by the processor, that the electrical shock has been delivered based on the change in the electrical current detected by the detection circuit.

18. The method of claim 16, further comprising:

determining, by the processor, a cumulative amount of energy delivered via the electrical shocks, wherein the second usability indication is further based on the cumulative amount of the energy delivered.

19. The method of claim 16, wherein:

the output device comprises a display; and the outputting comprises displaying the second usability indication via the display.

20. The method of claim 16, wherein:

the output device comprises a transmitter; and the outputting comprises transmitting the second usability indication via the transmitter to an external device for display of the usability indication on a display of the external device.

* * * * *